(12) United States Patent
Virtanen et al.

(10) Patent No.: US 8,773,229 B2
(45) Date of Patent: Jul. 8, 2014

(54) ELECTROMAGNET FOR LOW FIELD NMR MEASUREMENTS AND METHOD FOR MANUFACTURING THEREOF

(75) Inventors: Sami Virtanen, Espoo (FI); Jani Pakarinen, Kerava (FI)

(73) Assignee: Metso Automation Oy, Vantaa (FI)

( * ) Notice: Subject to any disclaimer, the term of this patent is extended or adjusted under 35 U.S.C. 154(b) by 0 days.

(21) Appl. No.: 13/819,961

(22) PCT Filed: Sep. 22, 2011

(86) PCT No.: PCT/FI2011/050817
§ 371 (c)(1),
(2), (4) Date: Feb. 28, 2013

(87) PCT Pub. No.: WO2012/038604
PCT Pub. Date: Mar. 29, 2012

(65) Prior Publication Data
US 2013/0154777 A1    Jun. 20, 2013

(30) Foreign Application Priority Data

Sep. 23, 2010   (FI) .................................. 20105980

(51) Int. Cl.
*H01F 5/00* (2006.01)
(52) U.S. Cl.
USPC ........................................... 335/299; 324/319
(58) Field of Classification Search
USPC ........... 335/216, 296–299; 324/309, 319, 320
See application file for complete search history.

(56) References Cited

U.S. PATENT DOCUMENTS

| | | |
|---|---|---|
| 4,800,354 A | 1/1989 | Laskaris |
| 5,138,326 A | 8/1992 | Edwards et al. |
| 5,659,277 A | 8/1997 | Joshi et al. |
| 6,275,365 B1 | 8/2001 | Kalsi et al. |
| 7,589,941 B2 | 9/2009 | Park et al. |
| 2007/0217097 A1 | 9/2007 | Park et al. |

FOREIGN PATENT DOCUMENTS

| | | |
|---|---|---|
| FR | 2 786 567 A1 | 6/2000 |
| GB | 444564 | 3/1936 |
| GB | 983528 | 2/1965 |
| GB | 2 162 641 A | 2/1986 |

OTHER PUBLICATIONS

Mar. 17, 2011 Finnish Search Report issued in Patent Application No. 20105980 (with translation).
Dec. 27, 2011 International Search Report issued in Patent Application No. PCT/FI2011/050817.
Jan. 10, 2013 International Preliminary Report on Patentability issued in Patent Application No. PCT/FI2011/050817.

*Primary Examiner* — Bernard Rojas
(74) *Attorney, Agent, or Firm* — Oliff PLC

(57) ABSTRACT

The invention relates to an electromagnet and a method manufacturing the same. The electromagnet includes a frame having a volume within, and a conductive wiring wound around the frame. In accordance with the invention the magnet includes at least two circular grooves having two walls parallel to the each other and perpendicular to the longitudinal axis of the frame, at least two wire stacks each including at least one substack, wherein the wire has a cross section, at least one of the walls separating the two circular grooves, and jump wiring interconnecting the stacks so that contributions from jump wires of the adjacent stacks to total axial directional current are cancelled in average by the current of the return current wire, such that their contribution to the resulting magnetic field at the sample volume is minimized.

15 Claims, 5 Drawing Sheets

ELECTROMAGNET FOR LOW FIELD NMR MEASUREMENTS AND METHOD FOR MANUFACTURING THEREOF

The invention relates to electromagnets suitable for low field NMR measurements such as determining the water content of a sample.

The invention also relates to an apparatus for adaptive pulse interval adjustment in NMR-based water content measurement.

NMR-technology (Nuclear Magnetic Resonance) has been used for determining moisture content of materials. For example FR 2786567 describes this kind of a system. Water content of various material samples can be measured accurately and rapidly using NMR relaxometry. Wide usage of NMR based moisture content measurement devices has been hindered mainly by the high cost, weight and size of magnets that produce the required homogeneous and strong enough main magnetic field. For many applications, e.g. biomass water content measurements, the desired sample volume is of the order of one liter or larger. Low cost compact NMR magnets that produce such a homogeneous and sufficiently strong field for a large enough volume have not been commercially available.

One reason for the large size is that the resistive electromagnets used to create a homogeneous magnetic field for NMR purposes typically consist of several conductor wire stacks relatively far from the sample volume. In such a way very high degree of homogeneity can be obtained with a moderate number of stacks, and wire positioning within the stacks and positioning of jump wiring is not especially critical. However, such a magnet structure has a poor efficiency regarding power consumption, and the magnet typically needs to be liquid cooled even in the low field regime. In addition, for such a construction the magnet size and weight are large compared to the homogeneous field volume.

It is an object of the present invention to provide a novel type of electromagnet for low field NMR-based water or other substance content measurements.

An object of one embodiment is to provide an electromagnet that is smaller than presently available alternatives.

Another object of one embodiment of the invention is to provide an electromagnet having a structure that makes it possible to construct the magnet within tight tolerance limits in order to achieve homogenous magnetic field in measurement volume.

One further object of some embodiments of the invention is to provide an electromagnet that can be structurally optimized to achieve desired level of homogeneity of the magnetic field in the measurement volume, and at the same time have a minimal power consumption for a given field strength and total mass of the conductor wiring. The energy efficiency is directly related to the maximum field strength achievable with the magnet.

Also an object of one embodiment is to provide an electromagnet that can be easily manufactured and assembled.

The invention is based on a magnet frame with an essentially cylindrical symmetry that has on its outer surface guiding grooves that accurately position the wire stacks of the magnet at least in the axial direction.

One embodiment is based on equalization of at least one dimension of the conductor wire in order to accurately position the wire loops in the radial direction.

One further embodiment of the invention is based on winding the wire of the wiring substacks alternatively in clockwise and counterclockwise directions to reduce the effect of effective radial currents to the field homogeneity.

One embodiment is based on routing the jump wires joining the wire stacks in a way that minimizes spurious effects to the field homogeneity at the sample volume inside the magnet frame. Such routing is enabled by alternating the winding direction of the wiring stacks.

Finally, the magnet provides a possibility to winding stacks with optimized radii and winding numbers to achieve a high level of energy efficiency and an optimized magnetic field in the measurement/sample volume.

More specifically, the electromagnet according to the invention and method for its manufacture is characterized by what is stated in the characterizing parts of the independent claims.

The invention offers significant benefits.

Bringing the conductor wire stacks closer to the sample volume according to the invention improves the energy efficiency and helps to make the magnet smaller and lighter, but also poses severe tolerance limits to conductor wire positioning and requires delicate wire routing to ensure high enough field homogeneity. This invention describes a magnet structure that guarantees precise positioning of the conductor wire stacks and a way to route the jump wiring so that its spurious effects to the field homogeneity are very small. The construction results in a combination of sample volume, magnet size and weight, energy efficiency and manufacturability that has not been available. Due to energy efficiency, the magnet does not need any forced cooling for field strengths corresponding to up to 1 MHz proton resonance in a measurement volume of approximately 1 dm3. The winding can be realized such that the magnetic field in the sample volume is determined to very high accuracy by only the current in the straight stack spiral wire segments, and contributions of current in the other sections of the wire are negligible.

In addition to above, the tolerances in the wire positioning can be made very small. The positioning of wire stacks themselves as well as single rounds of wire can be accurately set by mechanical structure of the magnet, whereby tight tolerances can be achieved by the structure of the magnet. This improves quality and diminishes danger of manufacturing errors.

In the following, the invention will be examined with the help of exemplifying embodiments illustrated in the appended drawings in which FIG. 1 presents schematically the basic conception of the frame of electromagnet.

FIG. 2a presents an assembled electromagnet.

FIG. 2b is a schematic view of a single wire stack.

FIG. 3a presents an enlargement of FIG. 2a.

Figure 1:
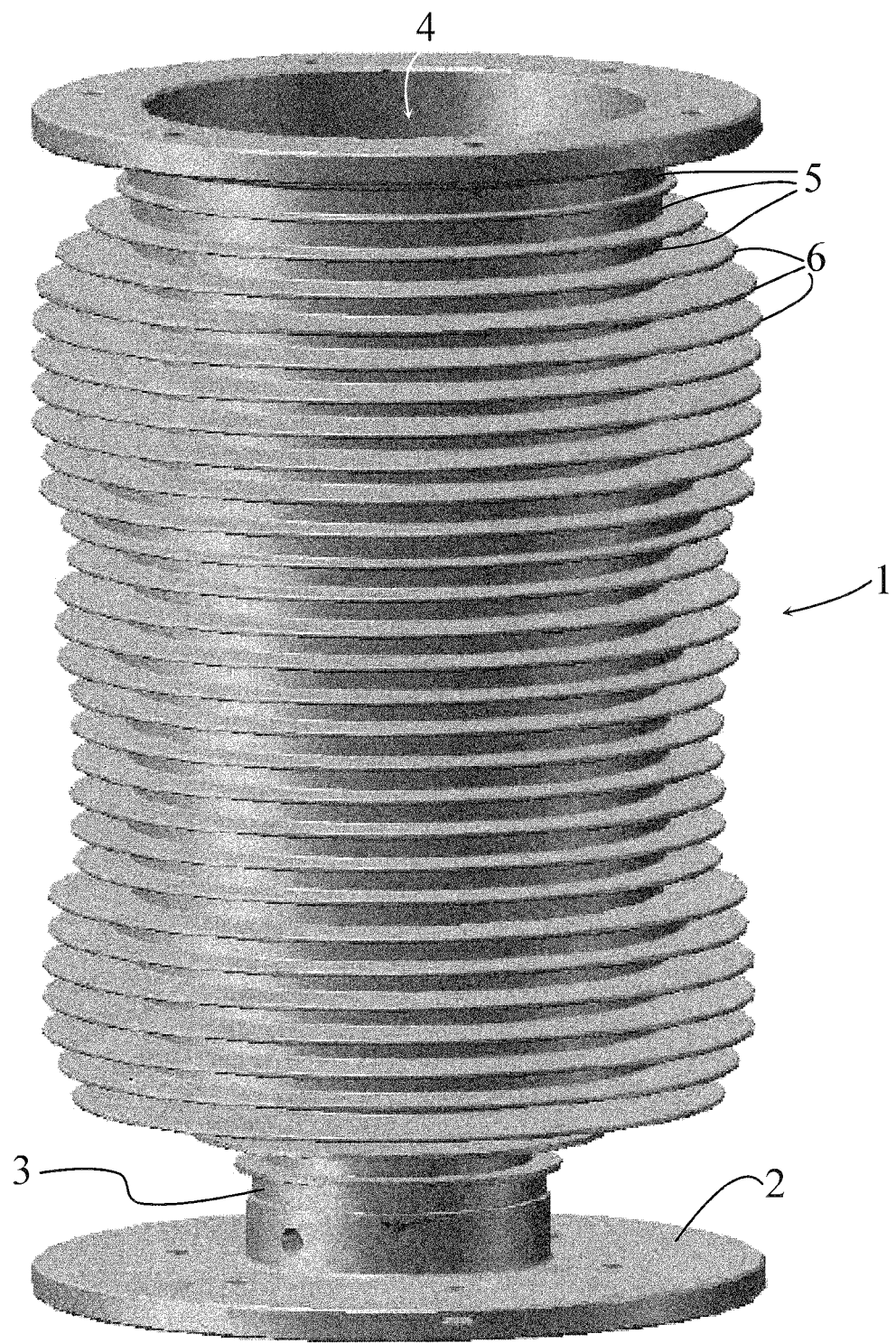
Figure 2A:
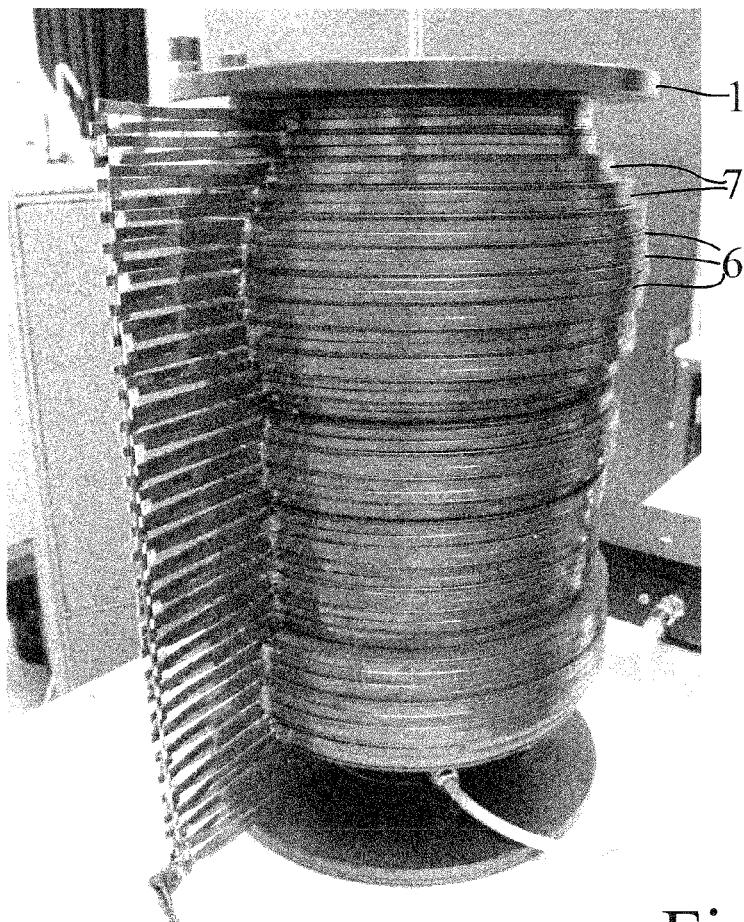
Figure 2B:
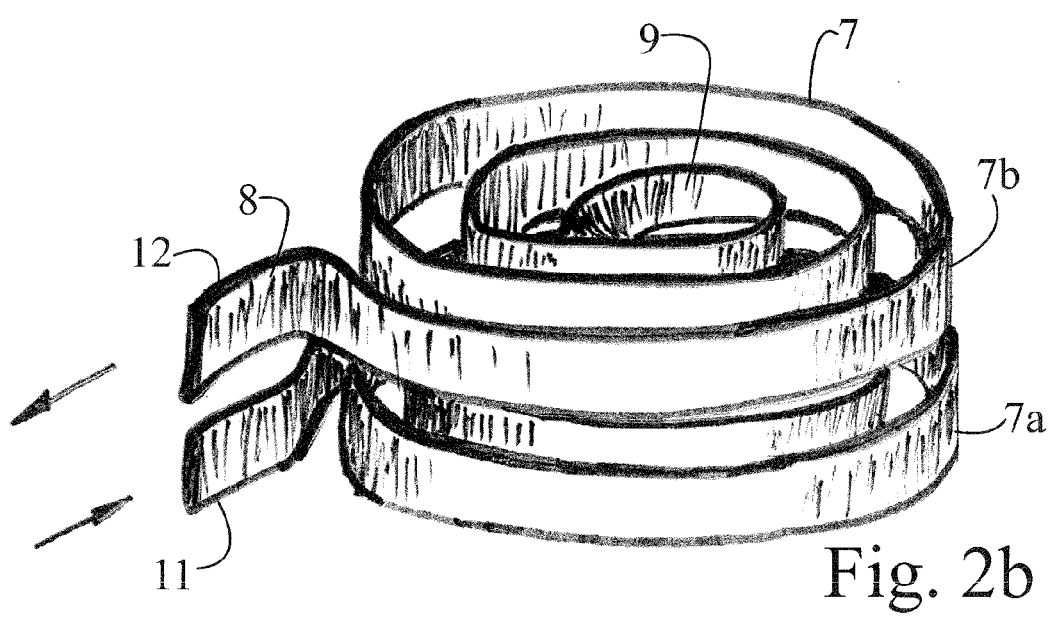

The frame 1 of the magnet is shown in FIG. 1. It comprises in this embodiment a base flange 2 for mounting the magnet in a standing position, a symmetrical cylindrical body 3 that has a cylindrical volume 4, for example for measuring moisture content of sample. The purpose of the electromagnet is to produce a highly homogeneous magnetic field into a cylindrical volume 4 that is relatively large compared to the overall size of the magnet. The cylindrical opening 4 in the frame contains the cylindrical sample volume space. In order to achieve a desired homogeneous magnetic field inside the cylindrical volume 4, a symmetrical cylindrical form is recommended. The magnet consists of the magnet frame 1 and the conductor wire. The conductor wire loops have to be wound accurately within tight tolerances around the frame 1 of the magnet in order to keep the homogeneity of the magnetic field inside the cylindrical volume on desired level. For achieving this, the body 3 of the frame 1 has N circular grooves 5 having a rectangular cross section shape, separated by N−1 separating walls 6. Now, each groove 5 is dimensioned to accommodate a wire stack 7 comprising two substacks 7a, 7b that are wound from a wire 8 that has a rectangular cross section. The wire forms two substacks 7a, 7b in each groove and in the groove bottom the wire forms one spiral loop 9 that connects the substacks 8. Other possible means of connecting the substacks include e.g. axially oriented pieces of conducting wire soldered to substacks in order to interconnect the bottom loops of the substacks. When a stack 7 is wound, the spiral loop 9 is first formed on the bottom of the stack groove 5, whereafter each substack 7a, 7b is wound by winding the conductor wire 8 in opposite directions until the stack groove 5 is filled or a predetermined number of rounds have been wound.

The tolerances for the positioning of the wire are quite tight in magnets used for NMR-measurements. In order to achieve a magnetic field homogeneous enough, a positional tolerance of approximately ±0.1 mm is required. Since there may be even tens of rounds of conductor wire on top of each other in a stack, the dimensional tolerance of the wire have to be very good if spatial position tolerance criteria is to be fulfilled over the whole length of the wire. Especially the thickness tolerance is critical. As the dimensional tolerances of commercially available leading wire and its covering insulator are too large for the tolerances required, a method for equalizing at least the thickness and flatness of the wire is needed.

Figure 4:
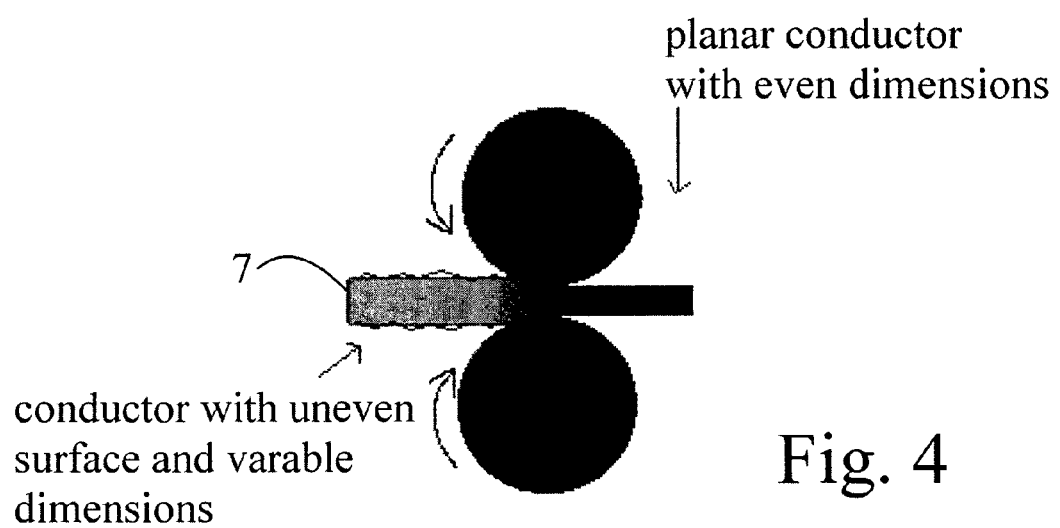
FIG. 4 shows equalization of the dimensions of a conducting wire.

In order to meet the above requirements, the wire has to be dimensionally equalized and planarized. This can be done efficiently by rolling the wire between two smooth accurately positioned rolls as shown in FIG. 4. Equalizing and planing by rolling is well established technology in metal working industry and here the same principle is applied to equalize the thickness of leading wire for the magnet. Usually treating only thickness is needed and width of the wire is suitable as delivered. An alternative method for equalization is chemical etching of the wire or the insulator, but this is not as effective as a manufacturing method and involves harmful substances. If really accurate positioning of the wire loops in a stack is desired, the thickness of the leading wire can be altered during winding in order to achieve a desired tolerance. Advantageously the rolling is performed after the insulator has been applied to the conducting wire, thus equalizing the thickness of, and planarizing also the insulator, the tolerances of which often are larger than the tolerances of the metal wire itself.

Figure 3A:
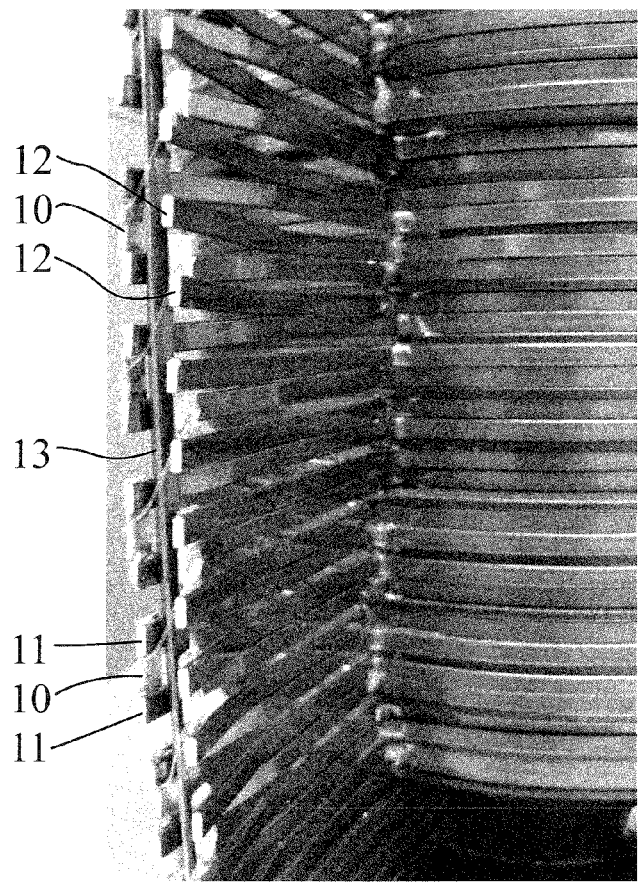
FIG. 3b shows graphically an arrangement of jump wires for leading the DC-current from adjacent stack to another.
Figure 3B:
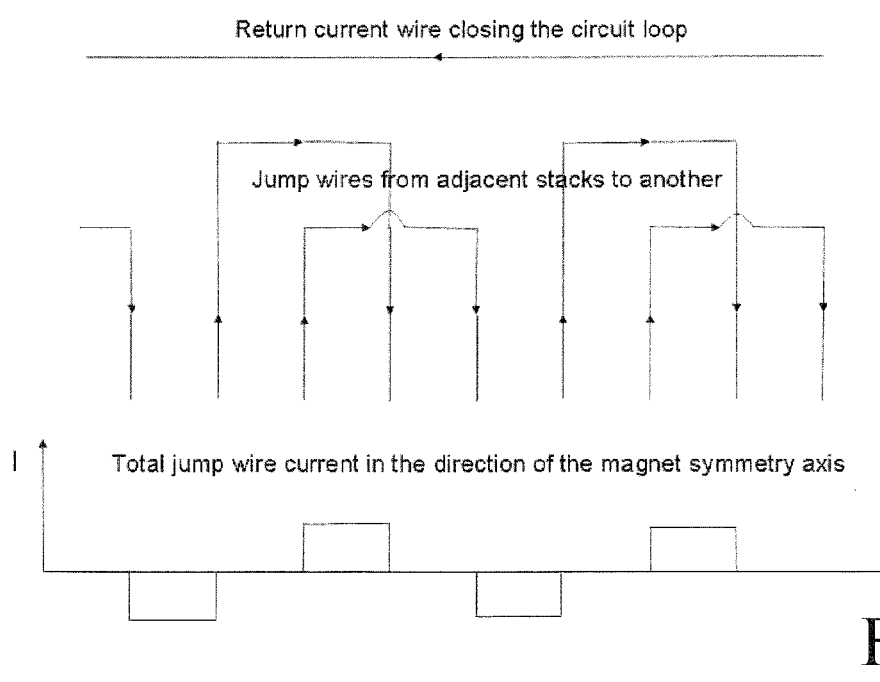

The positional accuracy in the axial direction is determined by grooves 5 and separating walls 7 of the magnet frame 1. Since these can be machined on the frame with great accuracy, the wire stacks are positioned accurately in the axial direction when the wire loops are pressed in the groove 5 during winding. After all of the wire stacks 7 are wound around the magnet frame 1, the electric circuit of the magnet is formed by joining the wire stacks 7 with jump wiring as illustrated in FIGS. 3a and 3b. The jump wiring is done by jump wire blocks 10; first substack 7a is connected through the jump wire block 10 to the first substack 7a of an adjacent wire stack by connecting the connection tongues 11 of the substacks 7a to each other. Similarly, the substacks 7b of adjacent wire stacks are connected to each other by a jump wire block 10. This is illustrated schematically in FIG. 3b. As can be seen in the FIG. 3b, the net averaged jump wire current in the axial direction is equal in magnitude but opposite in direction in respect to the current of the return current wire. Similarly, the axial effective current of the adjacent conductor stacks are cancelled by each other, since the stacks in the adjacent grooves are wound in opposite directions. Furthermore, the jump wire currents in the radial direction cancel each other between adjacent substacks.

One suitable mechanical structure for arranging the jump wiring is illustrated in FIG. 3a. Therein the connection tongues 11, 12 that are joined together are bent on a same direction forming a gap between each row of tongues and a return current wire 13 is positioned therebetween. Such a connection structure is simple to manufacture and electromagnetically advantageous, as discussed above.

The number of wire loops in the stacks, number of stacks and their radial distances from the symmetry axis of the frame 1 are optimized individually for each magnet according to its intended used. The radial distances $r(i)$, $i=[1, \ldots, N]$, of the groove roots from the symmetry axis of the magnet frame vary; the method to determine them is explained below.

The number of magnet frame grooves N, the width of the grooves w, the radial distances $r(i)$, $i=[1, \ldots, N]$, of the groove roots from the magnet frame symmetry axis and the winding numbers $Nw(i)$, $i=[1, \ldots, N]$, of stack spirals are determined computationally in such a way that the combination of sample volume, degree of magnetic field inhomogeneity in the sample volume, overall dimensions and weight of the magnet, power consumption, decay of the field outside the magnet and possible other relevant criteria are optimized by weighing them in a desired way.

The conductor wire is wound into the frame grooves in straight spiraling stacks and these stacks are connected in series to a current circuit in such a way that the following conditions are fulfilled:

1. The effective radial currents in adjacent substacks are directed opposite to each other, such that their contribution to the resulting magnetic field at the sample volume is minimized.
2. The interconnections of the stacks are arranged in such a way that contributions from the adjacent stacks to total axial directional current is cancelled by each other, such that the undesired contribution of the axial current to the resulting magnetic field at the sample volume is minimized. The adjacent stacks are advantageously wound in alternating directions.
2+. The interconnections of the stacks are arranged in such a way that contributions from the jump wires of adjacent stacks to total axial directional current is cancelled by the current in the return current wire, such that their contribution to the resulting magnetic field at the sample volume is minimized.
3. The groove separating walls and tight tolerances in the axial direction force the spiraling stacks to be straight and the stack planes to be orthogonal to the frame symmetry axis. The separating walls confine the conductor wire to the correct locations in the direction of the symmetry axis.

By fulfilling these conditions the winding can be realized such that the magnetic field in the sample volume is determined to very high accuracy by only the current in the straight stack spiral wire segments, and contributions of current in the other sections of the wire are negligible. In addition, the tolerances in the wire positioning can be made very small.

The number of substacks is not limited in two. When the number of substacks is even, the structure can be accomplished by simple addition to above described structure. Now separating walls are not placed between each stack but, for example after every third stack. This usually guarantees tight enough spatial tolerance in the direction of the symmetry axis of the magnet.

When the number of substacks is odd, some changes are needed in the structure. The essential difference to the above described embodiment is that part of the jump wiring is arranged to lead from stack to stack inside the magnet frame. This can be done by drilling holes to the magnet frame for the jump wires. In any case the topology of the jump wiring is otherwise very similar to that described above. Further, there is no inner spiral at the bottom of the stacks and against the magnet frame but the stacks are wound straight up from bottom. This is clearly an advantage in view of manufacturing. The downside is somewhat more difficult leading of jump wires inside the magnet.

Aluminum is an advantageous material for the magnet frame and wiring due to its relatively high thermal and electric conductivity combined with lightness and modest price. High thermal conductivity helps in minimizing thermal expansion gradients in the magnet. Of course, alternative conductive materials can be used, for example the traditional copper. However, the invention is not limited to any specific material and any suitable material that can be machined or otherwise formed to desired forms within required accuracy, can be used.

It is also conceivable to use a conductive wire that has another cross section than rectangular, for example round or oval. Then the bottom of the circular groove may follow the shape of the wire and the walls of the groove are parallel and perpendicular to the longitudinal axis of the frame. However, such an embodiment has some disadvantages. The electrical efficiency of the magnet is better the closer the sample volume the leading wires are positioned. If a round wire is used, free air space is left between the wires whereby part of the coil winding has to be positioned farther away from the sample volume if the cross section is intended to be kept invariable. Also the heat conductivity within the coil is decreased.

Figure 5:
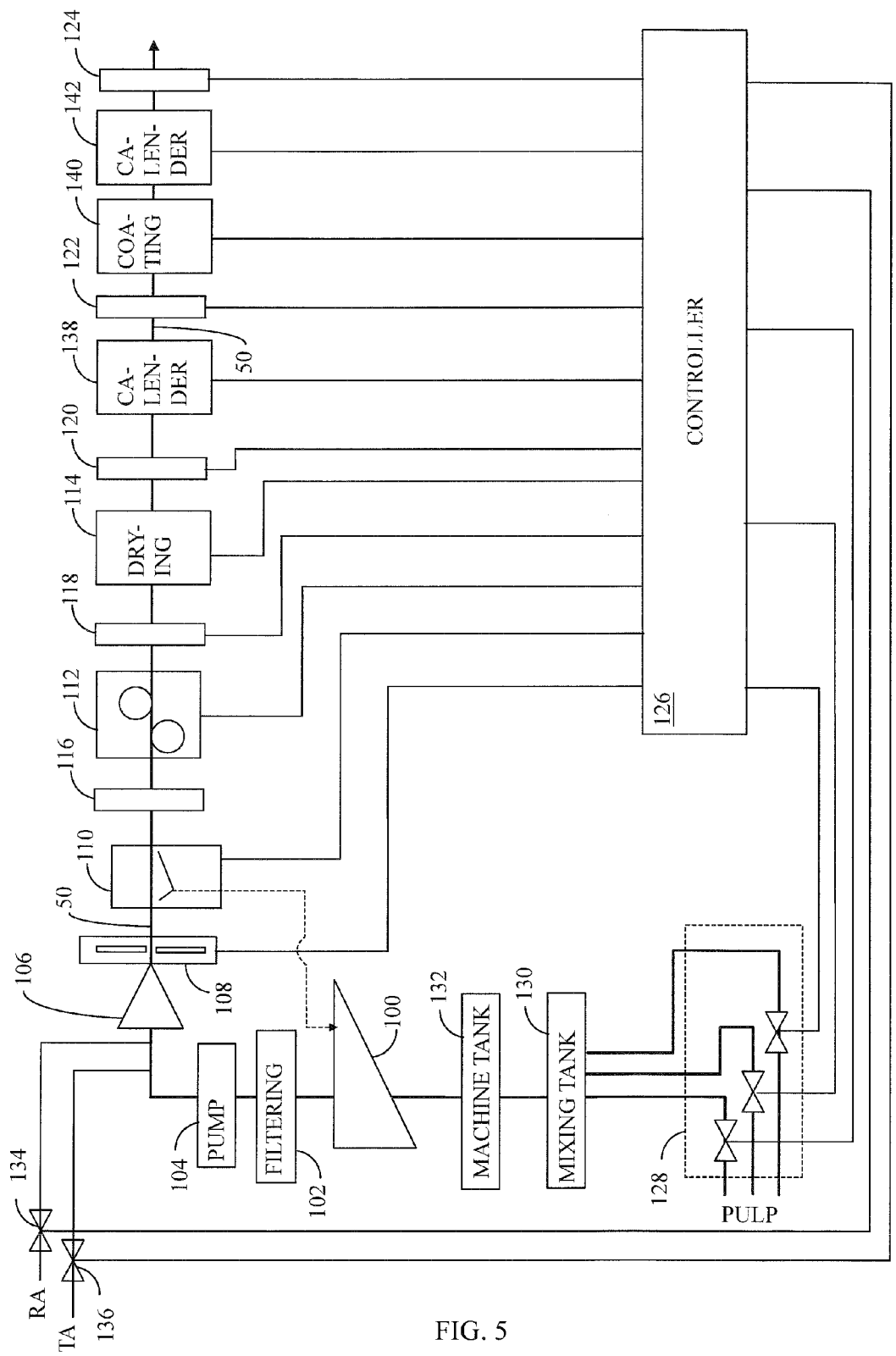
FIG. 5 shows a paper machine.

FIG. 5 shows the principle structure of a paper machine. A pulp flow or a plurality of pulp flows is/are fed into the paper machine through a wire pit 100, which is usually preceded by a mixing tank 130 for pulp flows and a machine tank 132. Machine pulp is batched for a short circulation by a weight control or a grade change program. The mixing tank 130 and the machine tank 132 may also be replaced by a separate mixing reactor (not shown in FIG. 5) and the batching of machine pulp is controlled by feeding each pulp flow separately by means of valves or some other flow control means 128. In the wire pit 100, the machine pulp is mixed with water to provide the short circulation (a broken line from a former 110 to the wire pit 100) with a desired consistency. From the pulp thus produced, it is possible to remove sand (hydrocyclones), air (deaeration tank) or other rough material (pressure screen) by cleaning equipment 102, and pulp is pumped by means of a pump 104 into a head box 106. Before the head box 106, if desired, a filler TA, such as kaolin clay, calcium carbonate, talc, chalk, titanium oxide, silica, etc., and/or a retention agent RA, such as inorganic, natural organic or synthetic water-soluble organic polymers may be added to the pulp. The filler may be used to improve formation, surface properties, opacity, brightness and printability and to reduce manufacturing costs. The retention agents RA, for their part, increase the retention of fines and fillers and simultaneously speed up the dewatering in a manner known per se. Both the fillers and the retention agents thus affect the surface topography of the web and the paper.

From the head box 106, the pulp is fed through a slice 108 of the head box into the former 110, which may be a four-drinier or a gap former. In the former 110, the web 50 is dewatered and ash, fines and fibres are removed into the short circulation. In the former 110, the pulp is fed as a web 50 onto the wire, and the web 50 is preliminarily dried and pressed in a press 112. The web 50 is primarily dried in a drying section 114. There is usually at least one measuring part 116 to 124 which may be electromagnets, by which for instance NMR measurements such as determining the water content of the web 50 can be performed.

A paper machine, which in this application refers to both paper and cardboard machines and also to pulp manufacturing machines, may also comprise, for instance, a precalender 138, a coating part/section 140 and/or a post-calender 142. However, there is not necessarily any coating section 140, and in that case there are not necessarily more than one calender 138, 142. In the coating section 140, a coating colour, which may contain for example kaolin, chalk or carbonate, starch, and/or latex, may be applied onto the paper surface. The use of coating colour usually reduces the roughness of the paper and improves glossiness.

In the calenders 138, 142, in which an uncoated or coated paper web travels between rolls that press with a desired force, the surface topography of the paper, such as roughness, can be changed. The calender 138, 142 may also affect the thickness and/or gloss of the paper. In the calender 138, 142, the properties of the paper web may be changed by moistening the web or by means of temperature and nip load/pressure between the rolls so that the greater the press applied to the web is, the smoother and glossier the paper will become. Moistening and an increase in the temperature further reduce roughness and improve glossiness. In addition, it is obvious that the operation of a paper machine is known per se to a person skilled in the art, wherefore it is not described in more detail in this context.

FIG. 5 also shows a control system for the paper machine. Factors affecting the quality and grade change include the amount and ratio of pulp flows, amount of filler, amount of retention agent, machine velocity, amount of backwater, moisture content of the web and drying capacity. A controller 126 may control the batching of pulp flows by means of valves 128, the batching of the filler TA by a valve 136, the batching of the retention agent RA by a valve 134, it may also control the size of the slice 108, the machine velocity, the amount of backwater and the drying process in block 114. The controller 126 also utilizes the measuring devices 116 to 120 for monitoring control measures, quality and/or grade change. The controller 126 may also determine the web 50 properties elsewhere (e.g. at the same points where controls are carried out).

The controller 126 may be considered as a control arrangement based on automatic data processing of the paper machine, or as a part thereof. The controller 126 may receive digital signals or convert the received analog signals to digital signals. The controller 126 may comprise a microprocessor and memory and process the signal according to a suitable computer program. The controller 126 may be based on a PID (Proportional-Integral-Derivative), MPC (Model Predictive Control) or GPC (General Predictive Control) control, for example.

What is claimed is:

1. An electromagnet comprising a frame and having a volume within, and a conductive wiring wound around the frame comprising:
the volume being a sample space,
at least two circular grooves having two walls parallel to the each other and perpendicular to the longitudinal axis of the frame,
at least two wire stacks in the grooves, each of the at least two wire stacks comprising
at least one substack wound with a wire, wherein the wire has a cross section, at least one of the walls separating the two circular grooves, and jump wires interconnecting the wire stacks so that contributions from the jump wires of the adjacent stacks to a total axial directional current are cancelled on average by the current of the return current wire, such that their contribution to the resulting magnetic field at the sample volume is minimized.

2. An electromagnet in accordance with claim 1, wherein, at least two wire stacks each comprise an even number of substacks and at least two substacks, and the substacks are wound in opposite directions.

3. An electromagnet in accordance with claim 1, wherein the at least two circular grooves have a rectangular cross section.

4. An electromagnet in accordance with claim 1, wherein at least the thickness of the wire is equalized.

5. An electromagnet in accordance with claim 1, comprising directing effective radial currents in adjacent stacks or stack pairs opposite to each other, such that their contribution to the resulting magnetic field at the sample volume is minimized.

6. An electromagnet according to claim 1, wherein the adjacent stacks or stack pairs are wound in alternating directions.

7. An electromagnet in accordance with claim 1, comprising arranging the interconnections of the stacks in such a way that contributions from jump wires of the adjacent stacks to total axial directional current are cancelled by the current of the return current wire, such that their contribution to the resulting magnetic field at the sample volume is minimized.

8. An electromagnet in accordance with claim 1, wherein the wire stacks are arranged in planes orthogonal to the frame symmetry axis.

9. A method for manufacturing an electromagnet, comprising:

forming a frame having a volume as a sample space within, and providing the frame with a conductive wiring comprising:
  forming at least two circular grooves having two walls parallel to each other and perpendicular to the longitudinal axis of the frame,
  winding at least two wire stacks in the grooves, each comprising at least one substack, wound with a wire, wherein the wire has a cross section,
  at least one of the walls separates the two circular grooves, and
connecting adjacent wire stacks together with jump wiring so that effective radial currents in adjacent stacks are directed opposite to each other, such that their contribution to the resulting magnetic field at the sample volume is minimized.

10. The method according to claim 9, wherein there are an even number of substacks, at least two substacks, wherein the wire has a cross section and the substacks are wound in opposite directions.

11. The method according to claim 10, comprising:
  forming at least two circular grooves having a rectangular cross section on the outer surface of the frame, and
  winding at least two wire stacks each comprising two substacks, wherein the wire has a rectangular cross section and the substacks are wound in opposite directions on the grooves of the frame.

12. A method in accordance with claim 10, including equalizing at least the thickness of the wire.

13. A method in accordance with claim 9, comprising arranging the interconnections of the stacks in such a way that contributions from adjacent stacks to a total axial directional current are cancelled on average by the current of the return current wire, such that their contribution to the resulting magnetic field at the sample volume is minimized.

14. A method according to claim 11, including equalizing at least the thickness of the wire by rolling.

15. A method according to claim 14, including equalizing at least the thickness of the wire by rolling after the applying of the insulator coating on the conductor wire.

* * * * *